United States Patent
Cooper et al.

(10) Patent No.: US 8,968,599 B2
(45) Date of Patent: Mar. 3, 2015

(54) GLASSY CHOLESTERIC LIQUID CRYSTALLINE METAL ACETYLIDES

(71) Applicant: The United States of America as represented by the Secretary of the Air Force, Washington, DC (US)

(72) Inventors: Thomas M. Cooper, Miamisburg, OH (US); Ronald F. Ziolo, Webster, NY (US); Aaron R. Burke, Vandalia, OH (US); Anatoliy V. Glushchenko, Colorado Springs, CO (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 107 days.

(21) Appl. No.: 13/780,153

(22) Filed: Feb. 28, 2013

(65) Prior Publication Data
US 2014/0242344 A1    Aug. 28, 2014

(51) Int. Cl.
C09K 19/36 (2006.01)
G02F 1/1333 (2006.01)
C07F 15/04 (2006.01)
C07F 15/00 (2006.01)
B32B 15/00 (2006.01)
B32B 15/04 (2006.01)
B32B 3/26 (2006.01)

(52) U.S. Cl.
CPC .......... C07F 15/0086 (2013.01); B32B 15/00 (2013.01); B32B 15/04 (2013.01); B32B 3/263 (2013.01)

USPC ............. 252/299.7; 349/182; 556/16; 556/22

(58) Field of Classification Search
USPC .......... 252/299.7; 428/1.1; 349/182; 556/16, 556/22
See application file for complete search history.

(56) References Cited

U.S. PATENT DOCUMENTS 7,355,057 B1   4/2008  Cooper et al.
8,124,299 B2   2/2012  Natarajan et al.

OTHER PUBLICATIONS

A. Jakli, "Chapter 6: Defect Structures" of One- and Two-Dimensional Fluids: Properties of Smectic, Lamellar, and Columnar Liquid Crystals, Taylor & Francis Group, New York, (2006) pp. 181-204.
S. H. Chen et al., "Glassy liquid crystal films as broadband polarizers and reflectors via spatially modulated photoracemization," Adv. Matls., vol. 11 (1999) 1183-1186.
T. M. Cooper et al., "Glass-forming liquid platinum acetylides," Chem. Matls., vol. 16 (2004) 3215-3217.
R. Eelkema et al., "Amplification of chirality in liquid crystals," Org. Biomol. Chem., vol. 4 (2006) 3729-3745.
T. M. Cooper et al., "Asymmetry in platinum acetylide complexes: confinement of the triplet exciton to the lowest energy ligand," J. Phys. Chem. A., vol. 110 (2006) 13370-13378.

(Continued)

*Primary Examiner* — Shean C Wu
(74) *Attorney, Agent, or Firm* — AFMCLO/JAZ; Chastity Whitaker

(57) ABSTRACT

A cholesteric liquid crystal. The liquid crystal includes a metal acetylide, of which the metal is a square, planar transition metal. The metal acetylide includes first and second acylphosphine ligands and first and second phenyl acetylene ligands. Each of the first and second phenyl acetylene ligands have a meta- or para-substituent, which are selected from the group consisting of H, F, CN, $OCH_3$, $C\equiv C-C_6H_5$, $(COO-C_{34}H_{50}O_2)$, and $COO-C_5H_{10}-C))-C_{34}H_{50}O_2$.

18 Claims, 13 Drawing Sheets

(56) References Cited

OTHER PUBLICATIONS

S. Pieraccini et al., "Chiral doping of nematic phases and its application to the determination of absolute configuration," Chirality, vol. 20 (2008) 749-759.

S. Pieraccini et al., "Chirality transfer across length-scales in neumatic liquid crystals: fundamentals and applications," Chem. Soc. Rev., vol. 40 (2011) 258-271.

J. Adams et al., "Cholesteric film as optical filters," J. Appl. Phys., vol. 42 (1971) 4096-4098.

N. Tamaoki, "Cholesteric liquid crystals for color information technology," Adv. Mater., vol. 13 (2001) 1135-1147.

S. J. Rzoska et al., "Complex dielectric relaxation in supercooling and superpressing liquid-crystalline chiral isopentylcyanobiphenyl," Phys. Rev. E., vol. 68 (2003) 031705.1-031705.9.

M. Massalska-Arodż, "Dielectric relaxation in the glass phase of a liquid cyrstal," Phys. Rev. B., vol. 47 (1993) 14552-14554.

I. Dierking, "Experimental investigations of a chiral smectic glass-forming liquid crystal," Liq. Cryst., vol. 35 (2008) 1015-1022.

R. Hou et al., "From smectic to columnar phase of polypedal liquid crystals based on tetrathiafulvalene/1,3-dithio-2-thione and cholesterol," Tetrahedron, vol. 67 (2011) 1238-1244.

S. H. Chen et al., "Glass liquid crystal films as broadband polarizers and reflectors via spatially modulated photoracemization," Adv. Mater., vol. 11 (1999) 1183-1186.

S. Furumi et al., "Glass-forming cholesteric liquid crystal oligomers for new tunable solid-state laser," Adv. Mater., vol. 22 (2010) 886-891.

H. P. Chen et al., "Glassy liquid crystal films with opposite chirality as high-performance optical notch filters and reflectors," Adv. Mater., vol. 12 (2000) 1283-1286.

N. S. S. Kumar et al., "Indane 1,3-diol and cholesterol-containing butadiene derivatives: photoresponsive liquid crystaline glasses for imaging applications," J. Photochem. Photobiol. A: Chem., vol. 207 (2009) 73-78.

P. V. Shibaev et al., "Lasing from chiral photonic band gap materials based on cholesteric glasses," Liq. Cryst., vol. 30 (2003) 1391-1400.

S. D. Jacobs et al., "Liquid-crystal laser optics: design, fabrication, and performance," J. Opt. Sci. Amer. B., vol. 5 (1988) 1962-1979.

T. J. Bunning et al., "Mid-wavelength IR(MWIR) polarizers from glassy cholesteric liquid crystals," Liq. Cryst., vol. 26 (1999) 557-565.

C. Kim et al., "Novel cholesteric glassy liquid cyrstals comprising benzene functionalized with hybrid chiral-nematic mesogens," Chem. Mater., vol. 20 (2008) 5859-5868.

K. A. Nguyen et al., "One- and two-photon spectra of platinum aceytlide chromophores: a TDDFT study," J. Phys. Chem. A., vol. 113 (2009) 13943-13952.

P. Van De Witte and Lub, J., "Optical components from a new vitrifying liquid crystal," Liq. Cryst., vol. 26 (1999) 1039-1046.

M. O'Neill et al., "Ordered materials for organic electronics and photonics," Adv. Mater. vol. 23 (2011) 566-584.

N. Tamaoki et al., "Photochemical phase transition and molecular realignment of glass-forming liquid crystals containing cholesterol/azobenzene dimesogenic compounds," Chem. Mater., vol. 15 (2003) 719-726.

R. K. Vijayaraghavan et al., "Photoresponsive glass-forming butadiene-based chiral liquid cyrstals with circularly polarized photoluminescence," Adv. Funct. Mater., vol. 18 (2008) 2510-2517.

K. S. Schanze, "Platinum acetylide materials for optical limiting," Final Report for Grant No. AFOSR F49620-03-1-0127 (2006) 13 pages total.

J. E. Rogers et al., "Platinum acetylide two-photon chromophores," Inorg. Chem., vol. 46 (2007) 6483-6494.

S. Furumi, "Recent progress in chiral photonic band-gap liquid crystals for laser applications," The Chem. Rec., vol. 10 (2010) 394-408.

A. A. Gevorgyan, "Reflection and transmission of light in medium/cholesteric/substrate and glass (1)/cholesteric/glass (2) systems," Tech. Phys., vol. 45 (2000) 1170-1176.

S. K. H. Wei et al. "Robust organic lasers comprising glassy-cholesteric pentafluorene doped with a red-emitting oligofluorene," Appl. Phys. Lett., vol. 94 (2009) 041111.1-041111.3.

K. S. Schanze, "Second generation organometallic materials for non-linear optical application," Final Report for Grant No. AFOSR FA9550-06-1-0184 (2009) 18 pages total.

H. Akiyama et al., "Synthesis, liquid-crystalline properties and photo-optical studies of photoresponsive oliomeric mesogens as dopants in a chiral glassy liquid crystal," Adv. Funct. Mater., vol. 16 (2006) 477-484.

J. E. Slagle et al., "Triplet excimer formation in a platinum acetylide," Preprint for Chemistry of Materials (2007) 21 pages total.

Y. A. Garbovskiy et al., "Tunable optical and nonlinear optical response of smectic glasses based on cobalt-alkanoates," Liq. Cryst., vol. 37 (2010) 1411-1418.

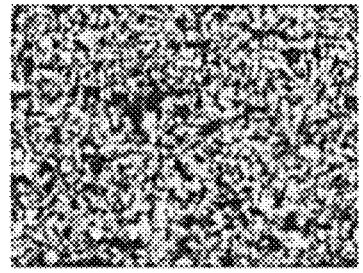
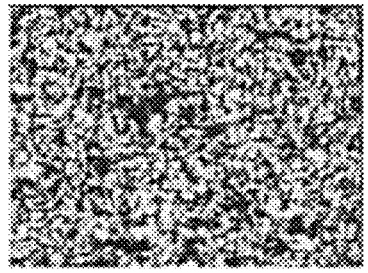
FIG. 6A  FIG. 6B
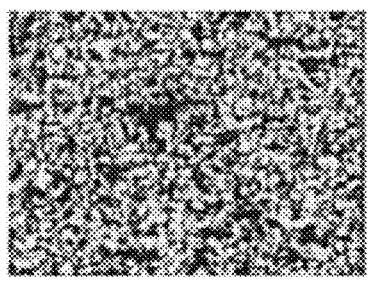
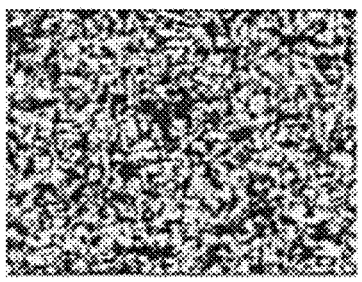
FIG. 6C  FIG. 6D
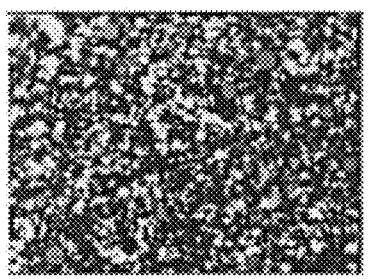
FIG. 6E  FIG. 6F
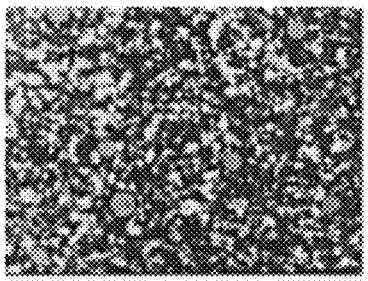
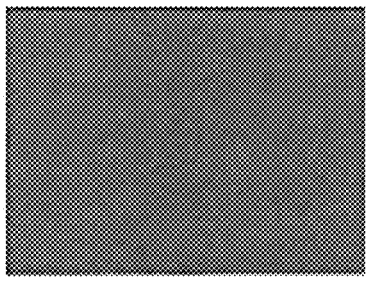
FIG. 6G  FIG. 6H

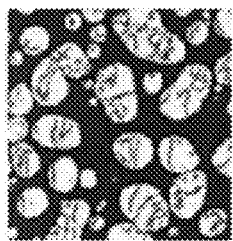
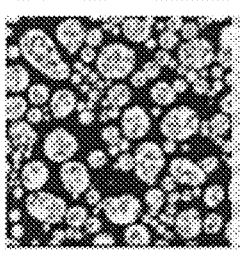
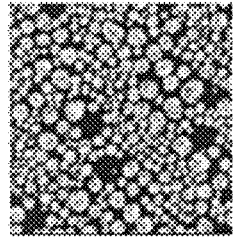
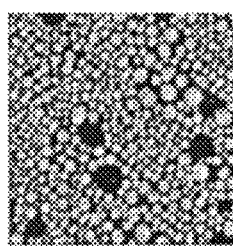
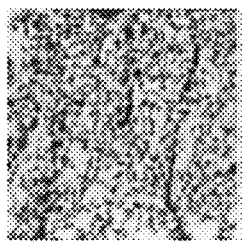
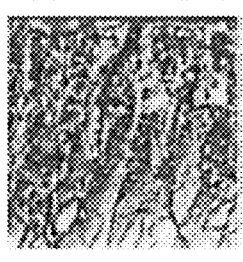
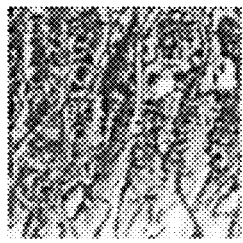
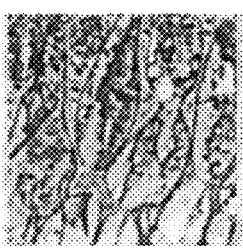
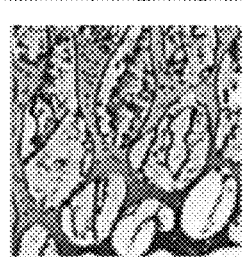
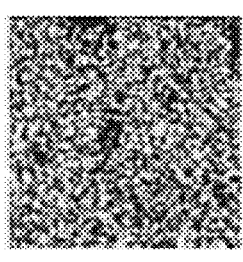
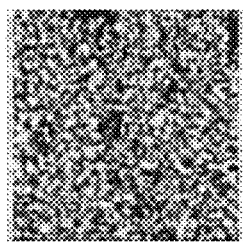
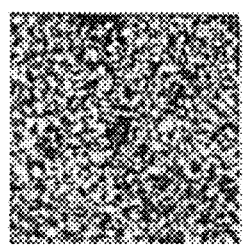
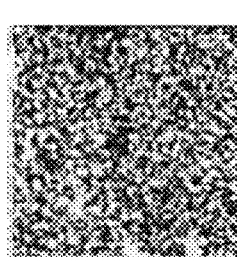

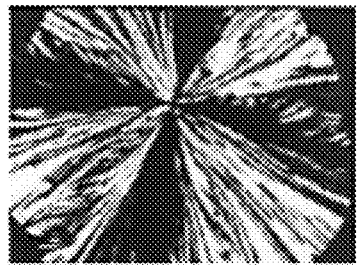
FIG. 12A    FIG. 12B
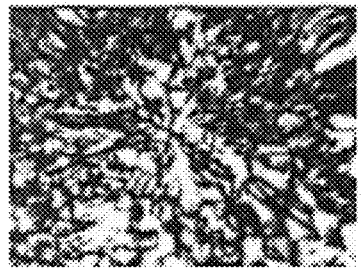
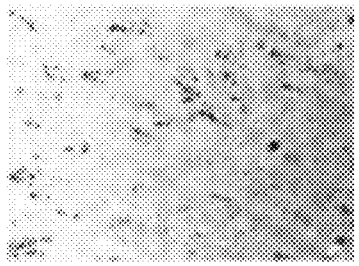
FIG. 12C    FIG. 12D
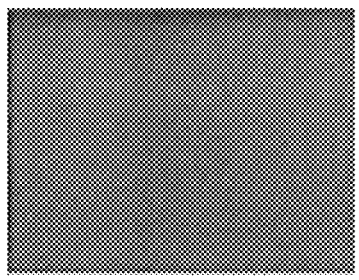
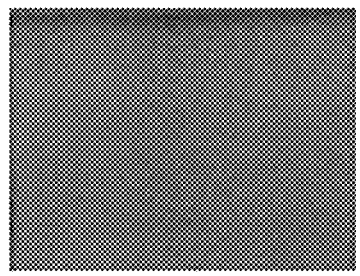
FIG. 12E    FIG. 12F

GLASSY CHOLESTERIC LIQUID CRYSTALLINE METAL ACETYLIDES

RIGHTS OF THE GOVERNMENT

The invention described herein may be manufactured and used by or for the Government of the United States for all governmental purposes without the payment of any royalty.

FIELD OF THE INVENTION

The present invention relates generally to cholesteric liquid crystals and, more particularly, to transition metal-based cholesteric liquid crystals.

BACKGROUND OF THE INVENTION

Crystal polarization optical elements (prism polarizers, wave-plates) have inherent limitations (costly, limited sizes, bulky, sensitive to the angle of incidence, limited to low optical power, low operating temperature, and restricted to use in visible spectral range), which prevent usage in some applications. Some elements have complicated structures, for example, regular circular polarizes include at least a linear polarizer and a one-quarter wave-plate, which are highly costly and require extra-holding mounts.

The use of liquid crystal based optical elements provides benefits to overcome most of these drawbacks. For example, cholesteric liquid crystal optical elements provide good optical quality at large apertures, high contrast with angular insensitivity, high transmission for passed polarization, environmental stability, laser-damage resistance, and back-reflection protection. Chiral dopants may be used to modify the optical properties of a nematic phase. However, in some cases, fluidity of liquid crystals is a serious obstacle, which may be overcome by using vitrified liquid crystals, e.g., liquid crystal glasses. Liquid crystal glasses are promising materials for developing optical elements. In particular, cholesteric crystal glasses are potentially useful as large area non-absorbing polarizers, optical notch filters, optically-switchable notch filters and reflectors, and polarizing fluorescent films. Moreover, cholesteric glassy films may serve as a one-dimensional photonic band-gap for circularly polarized lasing.

Yet, not all liquid crystalline materials may be used to form uniformly aligned anisotropic glasses stable. To be useful, the targeted materials must possess elevated phase transition temperatures, stability against crystallization from the glassy state, and selective reflection across the visible to near-infrared region. For example, Chol-OOC—$C_5H_{10}$—C≡C—C≡$C_5H_{10}$—COO-Chol has been reported to have a cholesteric glass transition temperature of 80° C. Cholesterol-containing butadienes show cholesteric phase at elevated temperatures, such as one example having a glass transition temperature of 89° C. Cyclohexane-based cholesteric liquid crystal glasses demonstrate a glass transition temperature of −65° C. Benzene functionalized with hybrid chiral-nematic mesogens are room temperature cholesteric glasses with a glass transition temperature 73° C. Cholesteric cyclosiloxanes have a glass transition temperature of 62° C. Nonetheless, there remain at least two main problems: time stability and uniform alignment over large surface areas.

Platinum acetylides have shown promise as nonlinear optical materials due to a high linear transmission, broadband triplet state spectra, and efficient conversion to the triplet state (due to the heavy atom effect of the central platinum atom). However, the full potential of platinum acetylides has not yet been achieved.

SUMMARY OF THE INVENTION

The present invention overcomes the foregoing problems and other shortcomings, drawbacks, and challenges of conventional liquid crystalline complexes, such as being costly, size limitations, bulky structures, angle of incidence sensitivity, limits on optical power, low operating temperature, and restricted to use in visible spectral range. While the invention will be described in connection with certain embodiments, it will be understood that the invention is not limited to these embodiments. To the contrary, this invention includes all alternatives, modifications, and equivalents as may be included within the spirit and scope of the present invention.

According to one embodiment of the present invention, a liquid crystal includes a metal acetylide, of which the metal is a square, planar transition metal. The metal acetylide includes first and second acyl-phosphine ligands and first and second phenyl acetylene ligands. The first and second phenyl acetylene ligands have first and second meta- or para-substituents, respectively, which are selected from the group consisting of H, F, CN, $OCH_3$, (COO—$C_{34}H_{50}O_2$), and COO—$C_5H_{10}$—COO—$C_{34}H_{50}O_2$.

Another embodiment of the present invention is directed to a method of forming the cholesteric liquid crystal by selecting a metal phosphine having a square, planar transition metal. The metal phosphine is reacted with the first phenyl acetylene ligand in a stoichiometric two-to-one ratio to form a half complex. The half complex is isolated and reacted with the second phenyl acetylene ligand in a two-to-one stoichiometric ratio to form the metal acetylide.

According to still another embodiment of the present invention, a liquid crystal cell includes first and second substrates forming a chamber therebetween. A volume of the cholesteric liquid crystal fills the chamber.

Yet another embodiment of the present invention is directed to a cholesteric liquid crystal compound having the formula:

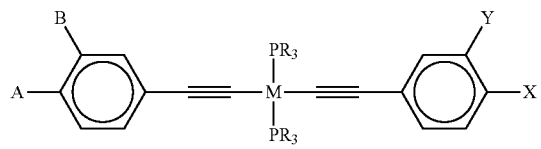

M is square, planar transition metal; R is selected from the group consisting of butyl ($C_4H_9$), ethyl ($C_2H_5$), or octyl ($C_8H_{17}$; M is chemically coupled to 3-Y,4-X-ethynyl benzene and 3B-4-A ethynyl benzene; and X is selected from the group consisting of hydrogen (H), fluorine (F), cyano (CN), methoxy ($OCH_3$), and 6-cholesteroloxy-6-oxohexyl-4-ethynylbenzoate (COO—$C_5H_{10}$—COO—$C_{34}H_{50}O_2$). A, B, and Y are each selected from the group consisting of hydrogen (H), cholesterol benzoate (COO—$C_{34}H_{50}O_2$), and 6-cholesteroloxy-6-oxohexyl-4-ethylbenzoate (COO—$C_5H_{10}$—COO—$C_{34}H_{50}O_2$).

According to another embodiment of the present invention, a high-temperature wedge for determining a cholesteric pitch of a liquid crystal includes a substrate and a silicon oxide layer on the substrate. The silicon oxide layer forms an angle with the substrate such that a cholesteric liquid crystal resides between the silicon oxide layer and the substrate.

Additional objects, advantages, and novel features of the invention will be set forth in part in the description which follows, and in part will become apparent to those skilled in the art upon examination of the following or may be leaned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and constitute a part of this specification, illustrate embodiments of the present invention and, together with a general description of the invention given above, and the detailed description of the embodiments given below, serve to explain the principles of the present invention.

FIGS. 6A-6H are 500 μm×750 μm resolution micrographs of the heating of a microscopy cell filled with a Metal-PEt$_3$ complex according to another embodiment of the present invention.

FIGS. 7A-7P are 500 μm×750 μm resolution micrographs of the cooling of the microscopy cell filled with the Metal-PEt$_3$ complex of FIGS. 6A-6H.

FIGS. 12A-12F are 900 μm×1200 μm resolution micrographs of the heating (FIGS. 12A-12E) and cooling (FIG. 12F) of a microscopy cell filled with a Metal-PEt$_3$ complex according to one embodiment of the present invention.

It should be understood that the appended drawings are not necessarily to scale, presenting a somewhat simplified representation of various features illustrative of the basic principles of the invention. The specific design features of the sequence of operations as disclosed herein, including, for example, specific dimensions, orientations, locations, and shapes of various illustrated components, will be determined in part by the particular intended application and use environment. Certain features of the illustrated embodiments have been enlarged or distorted relative to others to facilitate visualization and clear understanding. In particular, thin features may be thickened, for example, for clarity or illustration.

DETAILED DESCRIPTION OF THE INVENTION

A metal acetylide liquid crystalline complex according to one embodiment of the present invention includes a central, square planar transition metal, for example, platinum or palladium atom, with two acyl-phosphine ligands, a first phenyl acetylene ligand with meta- or para-substituent and a second phenyl acetylene meta- or para-cholesterol benzoate ligand, and having the structure:

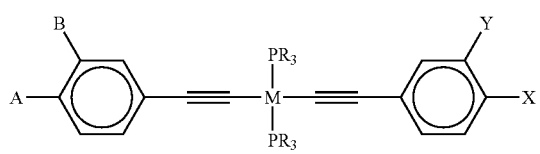

(hereafter referred to as "the Metal-PEt$_3$ complex"). According to some embodiments of the present invention, a first substituent X may include H, F, CN, OCH$_3$, C≡C-Phenyl, C$_5$H$_{11}$, or para-cholesterol benzoate. According to some embodiments of the present invention, second, third, and fourth substituents A, B, Y may include H or COO-cholesterol, wherein cholesterol is illustrated as "Chol" and has a structure of:

Chol =

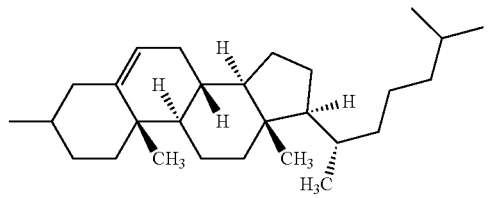

According to some embodiments of the present invention, phosphine substituents R may include methyl, ethyl, butyl and octyl. Substituents A, B, X, Y, R may be combined in any order, as would be understood by those of ordinary skill in the art having the benefit of the disclosure provided herein.

Figure 1:
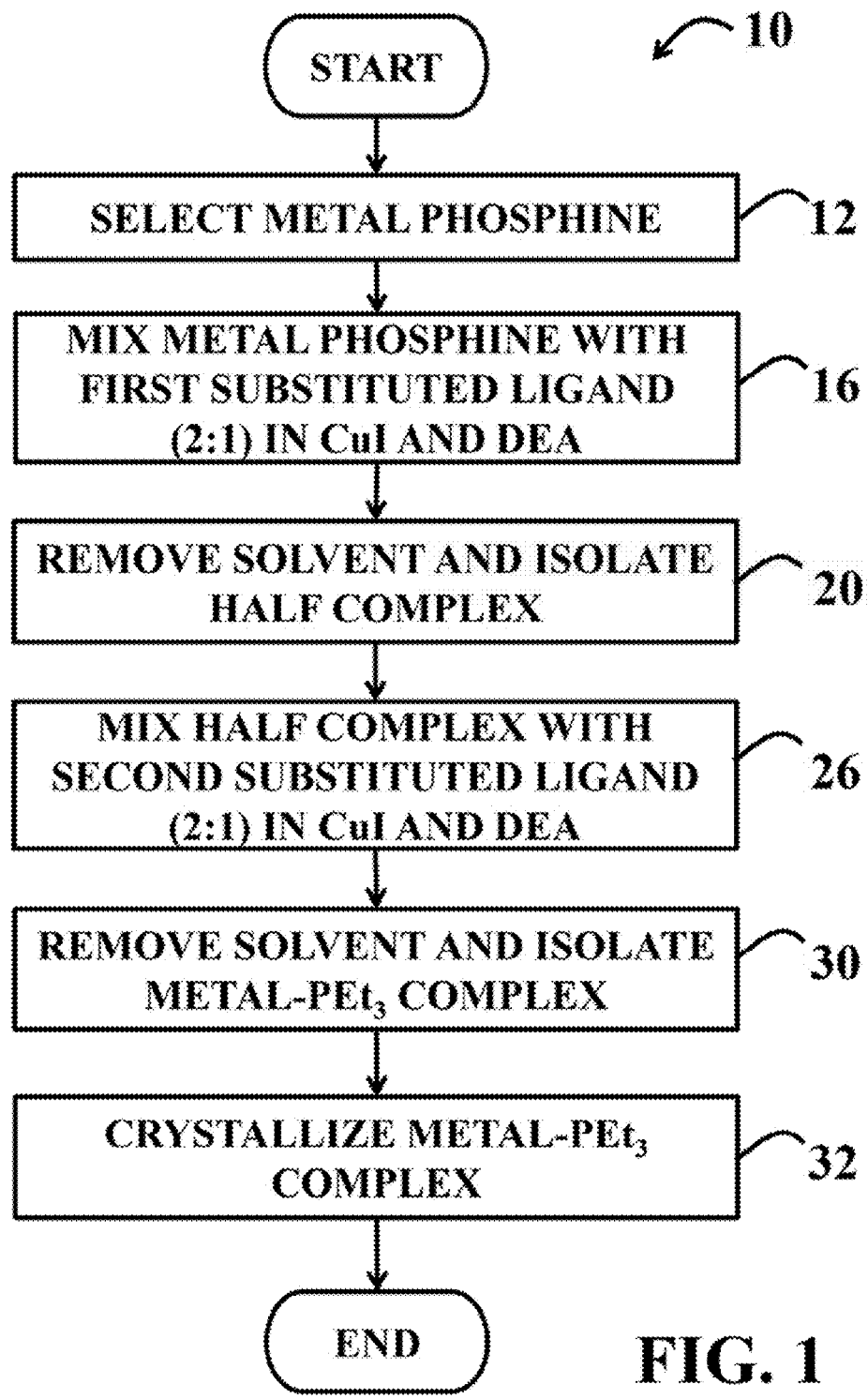
FIG. 1 is a flowchart illustrating a method of forming a Metal-PEt$_3$ complex according to an embodiment of the present invention.
Figure 2A:
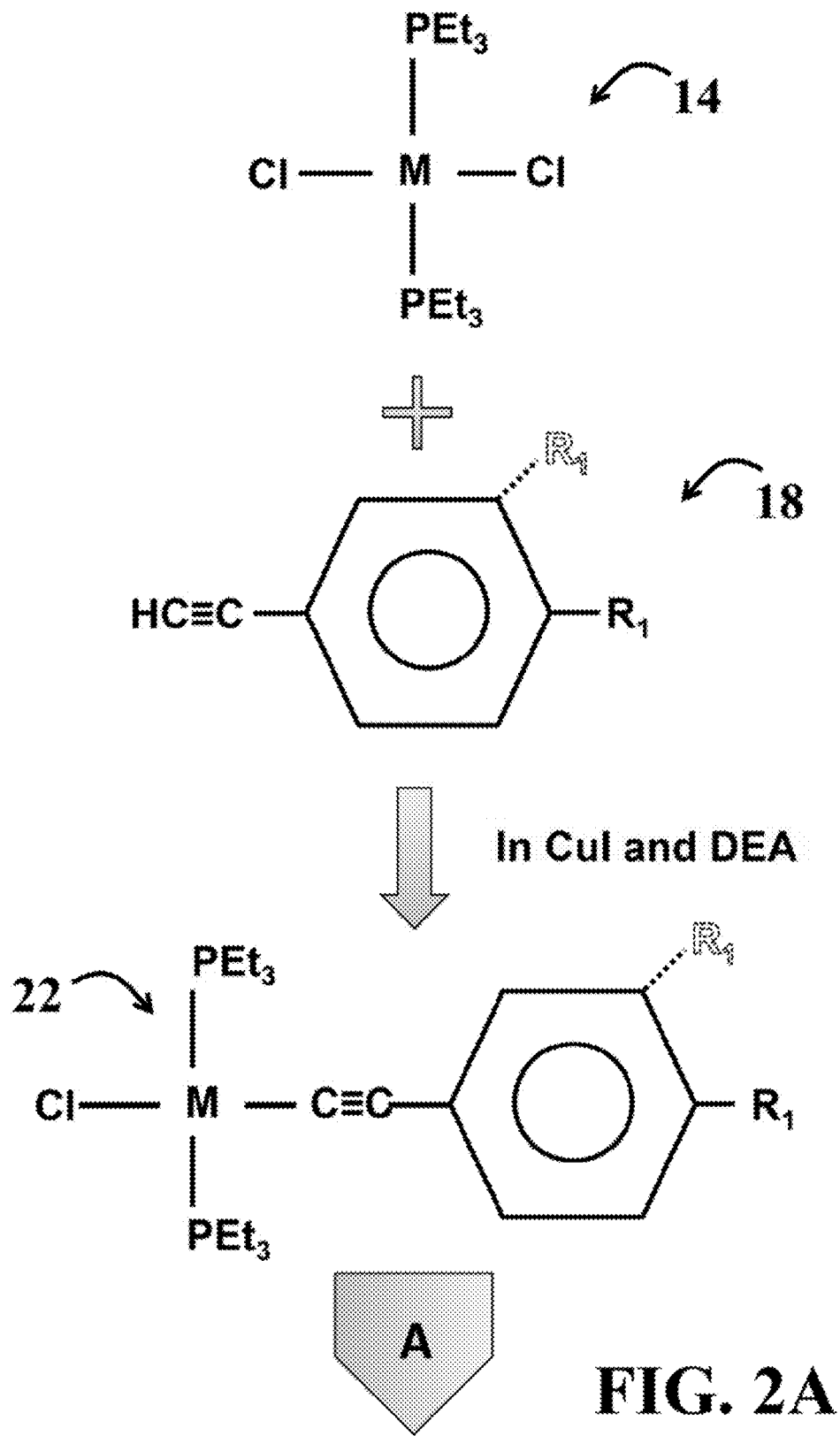
FIGS. 2A and 2B are schematic, chemical formula representations of the method of FIG. 1.
Figure 2B:
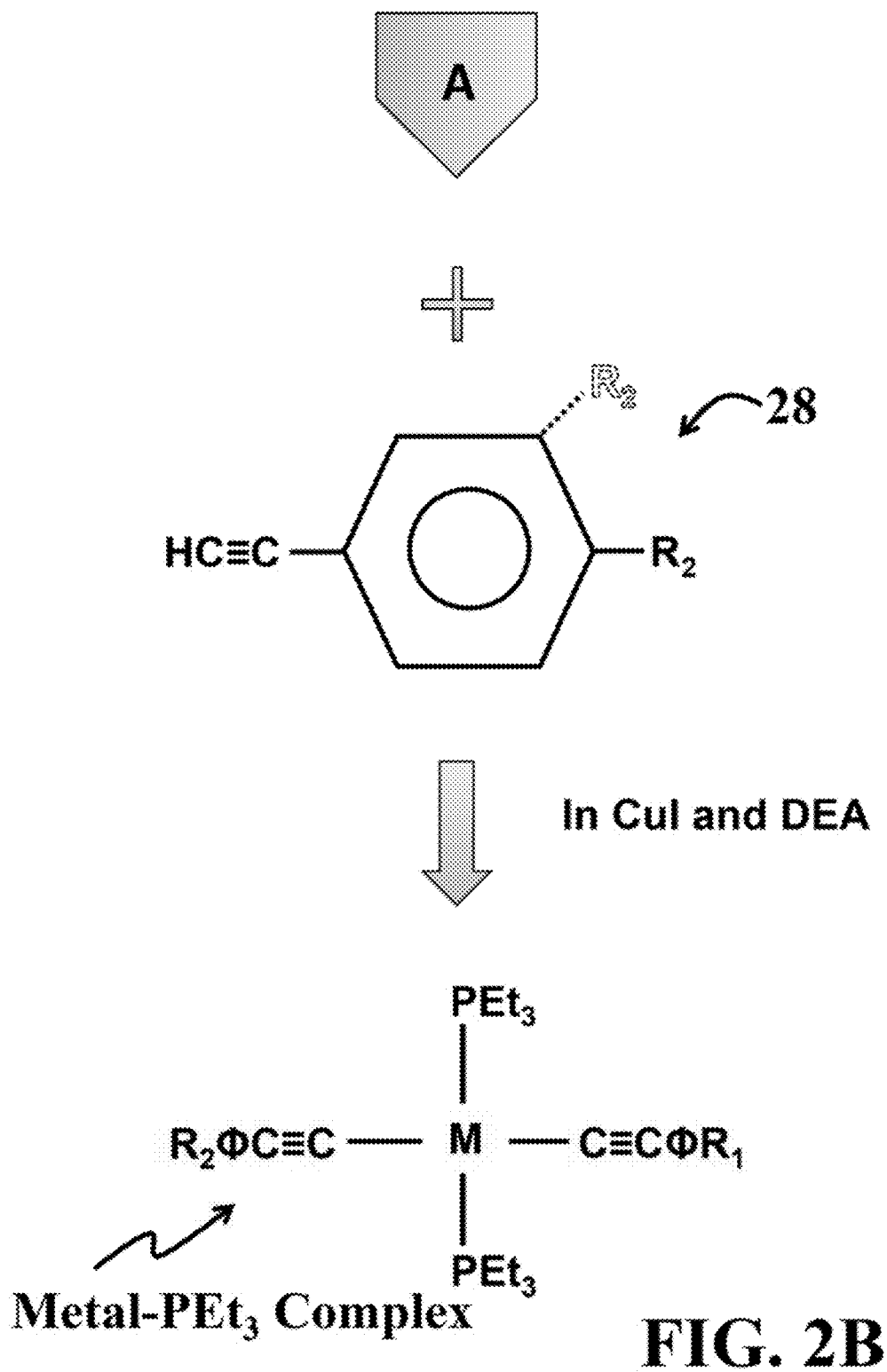

Preparation of the Metal-PEt$_3$ complex is shown in a flowchart 10 in FIG. 1 and schematically represented in the chemical equations of FIGS. 2A and 2B. Briefly, all reactions may be performed under standard laboratory pressures and temperatures, unless otherwise noted.

In Block 12, a metal phosphine 14, such as, but not limited to, [PEt$_3$]$_2$PtCl$_2$, is selected and mixed (Block 16) with a first substituted ligand 18 (2:1 stoichiometric ratio), for example, para-substituted H—CC(C$_6$H$_4$—R), wherein R may be H, CN, OCH$_3$, or CO$_2$-Chol, in a solution of cupreous iodine (CuI). One mole of diethyl amine solvent is added in a dropwise manner over a period of time, for example, 2 hours.

The mixture reacts, at room temperature, and the solvent removed (Block 20) by rotary evaporation at a slightly elevated temperature (for example, 30° C.). Resultant residue may be chromatographed on a silica gel column using dicholorontethane/hexane. A half-complex 22 may be separated from excess reactant material and a symmetrical PE-1 complex side product via chromatography, the PE-1 complex having the chemical formula:

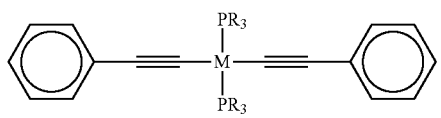

If desired, the mixture may be heated above room temperature while reacting, which leads to the promotion of a symmetrical product over an asymmetrical product, even with excess starting materials.

In Block 26, the half-complex may be added to an equimolar solution of CuI, diethyl amine, and a second substituted ligand 28, for example, para-substituted H—CC($C_6H_4$—R), wherein R may be $CO_2$-Chol or F. The mixture reacts at an elevated temperature (for example, 60° C.) and the solvent is removed (Block 30) by rotary evaporation at an elevated temperature (such as 55° C.). Resultant residue may be chromatographed on a silica gel column using dichloromethane/hexane. The Metal-$PEt_3$ complex (illustrated in FIG. 2B as the same) may be crystallized (Block 32) from a dichloromethane and methanol (DCM/MeOH) mixture once pure.

The structures of exemplary embodiments of the Metal-$PEt_3$ complex were confirmed via $^{31}P$ spectroscopy in deuterochloroform ($CDCl_3$). Generally, the $^{31}P$ spectra demonstrated an apparent "triplet," which actually is a singlet and a doublet. Phosphorus atoms of the Metal-$PEt_3$ complex were bound directly to the central platinum atom, of which 80% are non-spin active platinum atoms (yielding a singlet) and 20% are $^{195}Pt$ having a spin of ½ (yielding a singlet-centered doublet).

Some embodiments of the Metal-$PEt_3$ complex may be highly stable, with a glass transition temperature in the range of about 130° C. to about 135° C., as compared to conventional cholesteric glass transition temperatures ranging from about 60° C. to about 80° C.

Figure 3:
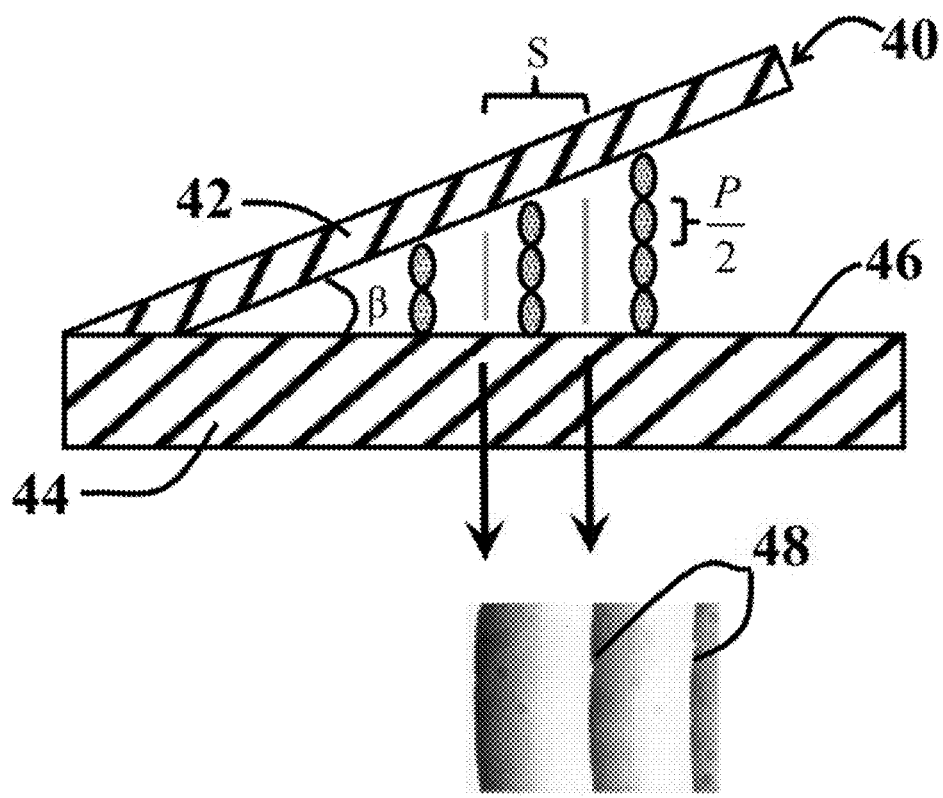
FIG. 3 is a diagrammatic view of a high-temperature wedge for measuring cholesteric pitch and a resultant polarized microscopy micrograph of a liquid crystal in the high-temperature wedge.

Metal-$PEt_3$ complexes, according to various embodiments of the present invention, may be monotropic and form cholesteric mesophases only under cooling. Metal-$PEt_3$ complexes according to other embodiments of the present invention may form a polycrystalline phase at room temperature.

turning now to FIG. 3, a high-temperature wedge 40 (i.e., a Grandjean-Cano wedge cell) configured for use in determining a cholesteric pitch of a liquid crystal is shown and described in accordance with one embodiment of the present invention. Conventionally, liquid crystal technologies are constructed from materials that fail at 200° C. However, the Metal-$PEt_3$ complexes, as described in accordance with embodiments of the present invention herein, require temperatures of about 250° C. for alignment. Accordingly, the high-temperature wedge 40 may be formed by oblique sputtering of an inorganic SiOx layer 42 onto a glass substrate 44 such that a cavity 46 having an opening angle, β, is formed. The inorganic materials, SiOx and glass, comprising the layer 42 and substrate 44 are sufficiently stable to sustain the glass transition temperatures of the Metal-$PEt_3$ complexes.

A cholesteric pitch of liquid crystals may be determined using the high-temperature wedge 40. For example, a Metal-$PEt_3$ complex according to an embodiment of the present invention may be loaded into the cavity 46, for example, via capillary action, heated to the glass transition temperature, and cooled. The cholesteric helix of the Metal-$PEt_3$ complex is grown perpendicular to the glass substrates due to planar boundary conditions.

As shown in FIG. 3, an integer number of half pitches (illustrated as "P/2") of the crystalline increases as the cavity increases, that is, the distance between the glass substrate 44 and the sputtered SiOx layer 42. The integer number increase in half pitches is observed with polarizing microscopy as disinclination lines 48 (i.e., Grandjean steps), which result from a disruption in the rotational symmetry of the grown crystal. Using a distance, S, between adjacent ones of the disinclination lines 48 and the opening angle, β, the cholesteric pitch, P, of the crystal may be determined by:

$P=(\tan \beta)(2S)$.

By varying the substituents A, B, X, Y, it is possible to tune the pitch of the cholesteric liquid crystal phase. For example, complexes in which A is COO-Chol, B is H, and Y is H, the pitch is 9.0 μm when X=F, the pitch is 3.4 μm when X=$OCH_3$, and the pitch is 3.5 μm X=CN.

The following examples illustrate particular properties and advantages of some of the embodiments of the present invention. Furthermore, these are examples of reduction to practice of the present invention and confirmation that the principles described in the present invention are therefore valid but should not be construed as in any way limiting the scope of the invention.

EXAMPLE 1

Compound I having a structure of:

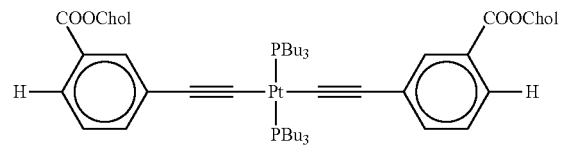

was synthesized in a closed, 250 ml round-bottom flask under normal laboratory atmosphere using of the shelf solvents with no further purification and in accordance with the one or more embodiments herein. The metal phosphine was $[PBu_3]_2PtCl_2$ (Sigma-Aldrich Chemical Co., St. Louis, Mo.), used without further purification, and the first and second substituted ligands were cholesterol 3-ethynyl benzoate (Chol-containing ligands courtesy of the Center for Applied Chemistry (Saltillo, M X, Dr. Eduardo Arias)).

NMR spectra were acquired on a 300 MHz NMR spectrometer (Varian, Palo Alto, Calif.) using deuterochloroform.

$^{31}P$ SPECTRUM: chemical shift of 230.5 Hz and a coupling constant of 2347.7 Hz.

$^1H$ SPECTRUM: 7.97(s, 2H), 7.20(d, J=7.8 Hz, 2H), 7.45 (d, J=7.8 Hz, 2H), 7.28(t, J=7.8 Hz, 2H), 5.45(d, J=3.6 Hz), 4.87(m, J=3.6 Hz), 2.48(d), 2.24–1.2(m), 1.10(s), 0.96(t, J=7.2 Hz), 0.90(d, J=7.2 Hz), 0.72(s).

13C SPECTRUM: 166.20, 139.92, 135.03, 132.05, 130.83, 129.38, 128.08, 126.23, 122.99, 109.81 ('false t,' J=14.6 Hz), 108.59, 74.61, 56.97, 56.43, 50.34, 42.59, 40.03, 39.81, 38.50, 37.34, 36.91, 36.48, 36.09, 32.21, 32.16, 31.87, 28.53, 28.28, 28.16, 26.67, 24.68 (t, J=7.1 Hz), 24.27(t, J=17.6 Hz), 24.13, 23.11, 22.94, 22.86, 21.34, 19.63, 19.02, 14.13, 12.14.

Figure 4:
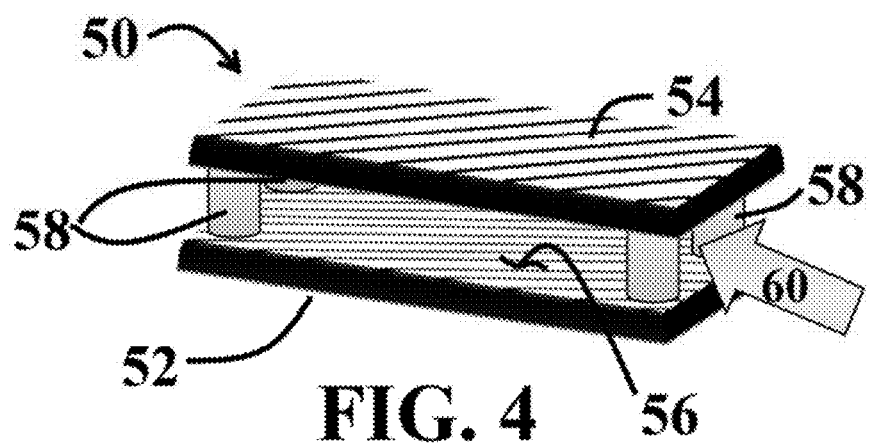
FIG. 4 is a perspective view of a cell configured for use in observing temperature-related behavior of a liquid crystal in accordance with an embodiment of the present invention.

Temperature-related characteristics of Compound I were evaluated using a cell 50, one embodiment of which is shown in FIG. 4. Generally, the cell 50 includes two glass substrates 52, 54, such as indium tin oxide (ITO), which are spin coated with a layer of polyimide (layer 56 shown for the first substrate 52) (20 s at 2,000 rpm), pre-baked (80° C. for 3 minutes to 5 minutes), and baked (180° C. for 1 hour). The polyimide layer was rubbed in anti-parallel directions with velvet cloth. Fiber spacers 58 (5 μm) were sputtered onto the polyimide layer 56 of the first substrate 52. The second substrate 54 was then clamped onto the spacers 58 and the first substrate 52 and sealed with UV-glue (not shown) (Norland Optical Adhesive 65, Norland Products, Inc., Cranbury, N.J.) to form a chamber therebetween, e.g., an empty cell. The empty cell, alongside powders of Compound I, was heated (for example, on a hot plate) above a melting temperature of Compound I, at which point Compound I melted and filled the cell via capillary forces (arrow 60). The cell and Compound I were observed during subsequent heating and cooling phases.

Using the foregoing, Compound I was found to be a crystalline solid, which melts to an isotropic phase at 231.2° C.

EXAMPLE 2

Compound II having a structure of:

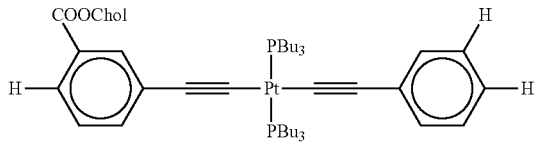

was synthesized in a manner similar to Example 1 above. The metal phosphine was $[PBu_3]_2PtCl_2$, the first substituted ligand was cholesterol 3-ethynyl benzoate, and the second substituted ligand was ethynylbenzene.

$^{31}P$ SPECTRUM: chemical shift of 514.0 Hz and a coupling constant of 2352 Hz.

$^1H$ SPECTRUM: 7.95(t, J=1.5 Hz, 1 H), 7.81(dt, J=8.0 Hz, J'=1.5 Hz, 1H), 7.65(m, J=22.3 Hz, J'=3 Hz, 1H), 7.45(dt, J=7.5 Hz, J'=0.12 Hz, 1H), 7.28(t, J=7.2 Hz, 2H), 7.23(t, J=6.6 Hz, 2H), 7.15(dt, J'=5.4 Hz, J'=1.5 Hz, 1 H), 5.45(d, J=3.6 Hz), 4.86(m, J=3.6 Hz), 2.48(d), 2.24–1.2(m), 1/10(s), 0.96(t, J=7.2 Hz), 0.90(d, J=7.2 Hz), 0.72(s).

$^{13}C$ SPECTRUM: 166.31, 139.98, 135.11, 132.03, 131.14, 131.03, 130.80, 129.45, 129.29, 129.06. 128.10, 126.15, 125.08, 122.99, 110.21('false t,' J=14.6 Hz), 109.22, 108.49, 107.97('false t,' J=14.6 Hz), 74.63, 68.41, 56.96, 56.40, 50.31, 42.59, 40.01, 9.78, 38.98, 38.38, 37.31, 36.91, 36.45, 36.07, 32.20, 32.15, 30.62, 29.18, 28.50, 28.28, 28.14, 26.78, 26.49, 24.67(t, J=7.1 Hz), 24.09(t, J=17.6 Hz), 23.95, 23.25, 23.09, 22.83, 21.31, 19.62, 18.98, 14.10, 12.13.

Using the cell described in Example 1, Compound II was found to be a crystalline solid, which melts to an isotropic phase at 121.6° C.

EXAMPLE 3

Compound III having a structure

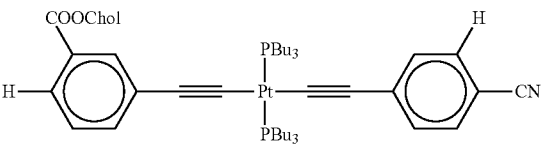

was synthesized in a manner similar to Example 1 above. The metal phosphine was $[PBu_3]_2PtCl_2$, the first a substituted ligand was cholesterol 3-ethynyl benzoate, and the second substituted ligand was 4-ethynylbenzonitrile.

$^{31}P$ SPECTRUM: chemical shift of 540.9 Hz and a coupling constant of 2332.8 Hz.

$^1H$ SPECTRUM: 7.95(s, 1H), 7.82(d, J=7.8 Hz, 1H), 7.50 (d, J=7.8 Hz, 2H), 7.44(d, J=7.8 Hz, 1H), 7.31(d, J=7.8 Hz, 2H), 7.28(d, J=7.8 Hz, 1H), 5.44(d, J=4.2 Hz), 4.87(m, J=4.2 Hz), 2.47(d), 2.24-1.2(m), 1.09(s), 0.95(t, J=7.2 Hz), 0.90(s), 0.88(s), 0.72(s).

$^{13}C$ SPECTRUM: 166.22, 139.92, 135.06, 134.12, 132.01, 131.33, 130.85, 129.15, 128.14, 126.38, 123.03, 119.88, 117.77('false t,' J=14.3 Hz), 109.00('false t,' J=14.5 Hz), 108.99, 107.69, 74.67, 56.95, 56.39, 50.30, 42.58, 40.00, 39.78, 38.48, 37.31, 36.91, 36.45, 36.07, 32.20, 32.14, 28.51, 28.28, 28.14, 26.62, 24.66(t, J=6.8 Hz), 24.22(t, J=17.1 Hz), 24.09, 23.10, 22.84, 21.31, 19.62, 18.99, 14.09, 12.13.

Figure 5A:
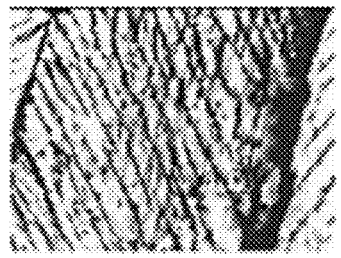
FIGS. 5A-5F are 900 μm×1200 μm resolution micrographs of the heating (FIGS. 5A-5C) and cooling (FIGS. 5D-5F) of a microscopy cell filled with a Metal-PEt$_3$ complex according to one embodiment of the present invention.
Figure 5B:
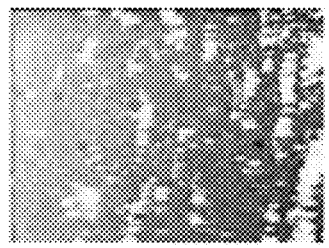
Figure 5C:
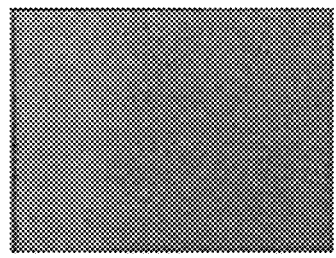
Figure 5D:
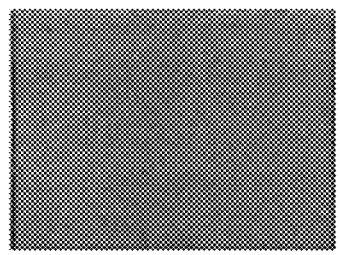
Figure 5E:
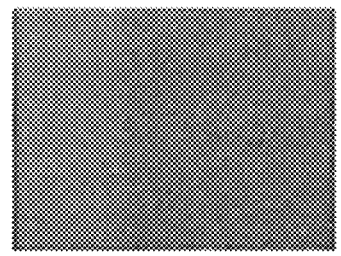
Figure 5F:
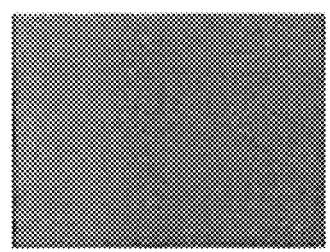
Figure 8A:
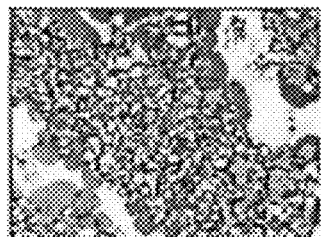
FIGS. 8A-8O are 500 μm×750 μm resolution micrographs of the heating of a microscopy cell filled with a Metal-PEt$_3$ complex according to another embodiment of the present invention.
Figure 8B:
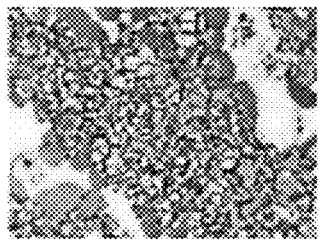
Figure 8C:
Figure 8D:
Figure 8E:
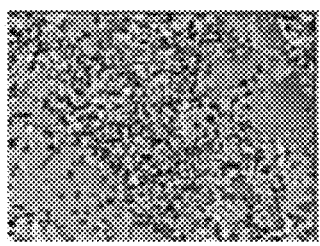
Figure 8F:
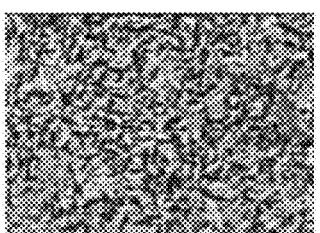
Figure 8G:
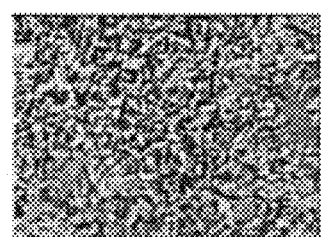
Figure 8H:
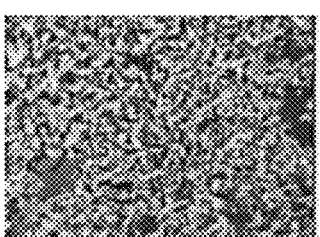
Figure 8I:
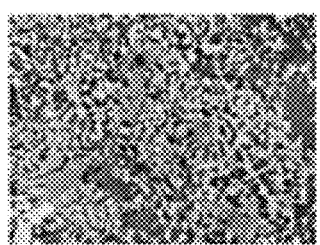
Figure 8J:
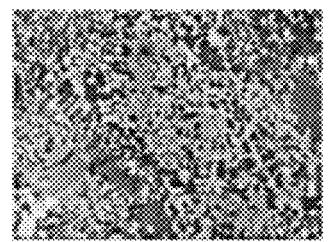
Figure 8K:
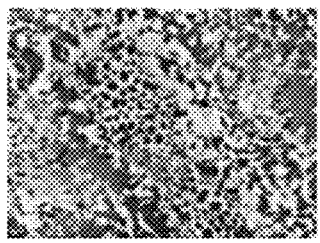
Figure 8L:
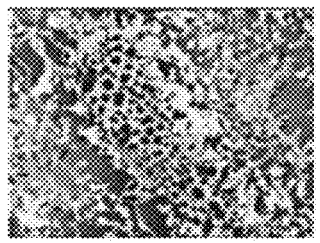
Figure 8M:
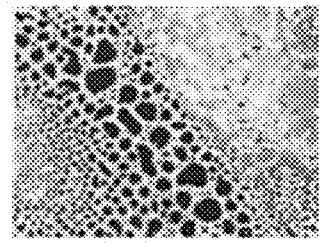
Figure 8N:
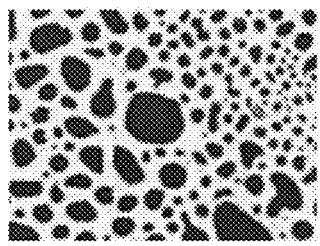
Figure 8O:
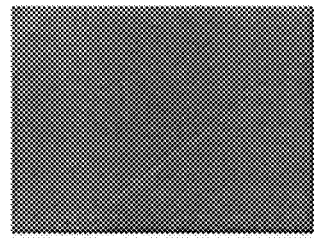
Figure 9A:
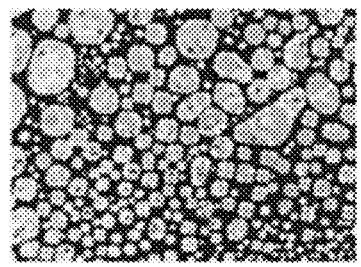
FIGS. 9A-9G are 500 μm×750 μm resolution micrographs of the cooling of the microscopy cell filled with the Metal-PEt$_3$ complex of FIGS. 8A-8O.
Figure 9B:
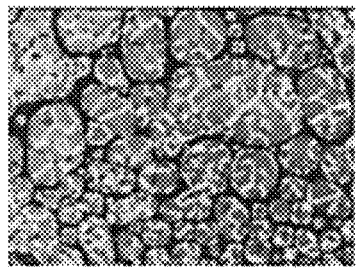
Figure 9C:
Figure 9D:
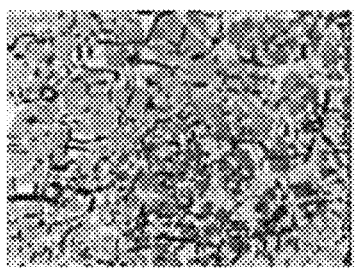
Figure 9E:
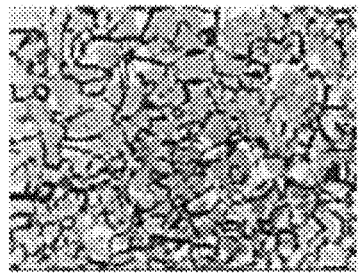
Figure 9F:
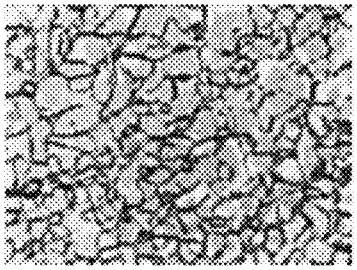
Figure 9G:
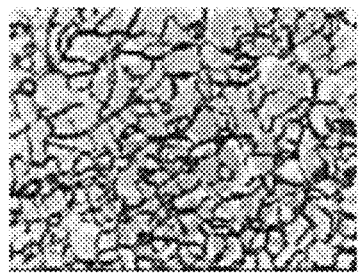

Using the cell described in Example 1, Compound III was found to exhibit a polycrystalline phase at room temperature (FIG. 5A). As the temperature increased, the polycrystaline phase melted (about 170° C., FIG. 5B) and, at 180° C., melting to an isotropic liquid was complete (FIG. 5C). On cooling to room temperature, Compound III showed isotropic texture (FIGS. 5D-5F).

EXAMPLE 4

Compound IV having a structure

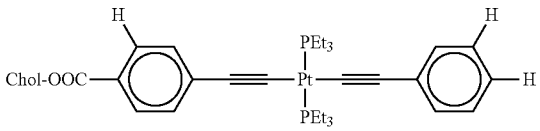

was synthesized in a manner similar to Example 1 above. The metal phosphine was $[PBu_3]_2PtCl_2$, the first a substituted ligand was cholesterol 4-ethynyl benzoate, and the second substituted ligand was ethynylbenzene. The percent yield of the half complex was 33.5%, and the percent yield of Compound IV was 55.5%.

$^{31}P$ SPECTRUM: chemical shift of 1482.7 Hz and a coupling constant of 2357.8 Hz.

$^1H$ SPECTRUM: 7.92(d, J=8.1 Hz, 2H), 7.32(d, J=8.4 Hz, 2H), 7.32(d, J=8.4 Hz, 2H), 7.26(t, J=7.5 Hz, 2H), 7.16(d, J=7.2 Hz, 1H), 5.45(d, J=3.6 Hz), 4.86(m), 2.48(d), 2.20(m, J=3.6 Hz, 12H), 1.25(m, J=8.4 Hz, 15H), 1.10(s), 0.96(d), 0.90(dd, J=1.5 Hz, J=6.6 Hz), 0.72(s).

$^{13}C$ SPECTRUM: 166.32, 140.02, 133.83, 131.13, 130.83, 129.56, 128.93, 128.22, 127.11, 125.43, 122.96, 114.04 ('false t,' J=14.1 Hz), 110.07, 109.97, 107.10('false t,' J=14.1 Hz), 74.55, 56.96, 56.39, 50.30, 42.59, 40.01, 39.79, 38.53, 37.32, 36.92, 36.46, 36.09, 32.21, 32.14, 29.53, 28.32, 28.18, 24.57, 24.11, 23.13, 22.86, 21.33, 19.67, 19.00, 16.61 (t, J=17.6 Hz), 12.15, 8.64.

Using the cell described in Example 1, Compound IV was found to exhibit a crystalline solid at room temperature, which melted to an isotropic phase at temperatures ranging from about 120° C. to about 200° C.

EXAMPLE 5

Compound V having a structure

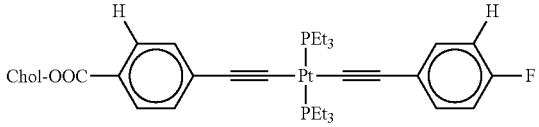

was synthesized in a manner similar to Example 1 above. The metal phosphine was $[PBu_3]_2PtCl_2$, the first a substituted ligand was cholesterol 4-ethynyl benzoate, and the second substituted ligand was 4-ethynylfluorobenzene. The percent yield of the half complex was 20.7%, and the percent yield of Compound V was 62%.

$^{31}$P SPECTRUM; chemical shift of 1482.7 Hz and a coupling constant of 2359.6 Hz.

$^{1}$H SPECTRUM: 7.92(d, J=8.7 Hz, 2H), 7.32(d, J=8.4 Hz, 2H), 7.26(d, J=8.7 Hz, 1H), 7.24(d, J=8.7 Hz, 1H), 6.94(d, J=8.7 Hz, 1H), 6.91(d, J=8.7 Hz, 1H), 5.44(d, J=3.9 Hz), 4.85(m), 2.48(d), 2.19(m, J=3.6 Hz, 12H), 1.25(m, J=8.1 Hz, 15 Hz), 1.09(s), 0.95(d), 0.90(dd, J=6.6 Hz, J=1.2 Hz), 0.72(s).

$^{13}$C SPECTRUM: 166.28, 160.94(d, J=245.3 Hz), 140.0, 133.81, 132.50(d, J=8.0 Hz), 130.81, 129.55, 127.13, 124.99, 122.96, 115.20(d, J=21.7 Hz), 113.87('false t,' J=14.6 Hz), 109.90, 108.71, 106.50('false t,' J=14.3 Hz), 74.54, 56.96, 56.39, 50.30, 42.58, 40.01, 39.79, 38.53, 37.25, 36.91, 36.46, 36.08, 32.20, 32.14, 28.52, 28.30, 28.18, 24.57, 24.11, 23.18, 22.86, 21.32, 19.66, 19.00, 16.61 (t, J=17.6 Hz), 12.14, 8.62.

Using the cell described in Example 1, Compound V was found to exhibit a noncrystalline phase at room temperature (FIG. 6A). As the temperature increased, the polycrystalline structure melted (about 175° C., FIGS. 6B-6D) and, at about 220° C., melting to an isotropic liquid was complete (FIG. 6H).

FIGS. 7A-7P illustrate cooling of Compound V. On cooling, a cholesteric phase appeared at about 188.2° C. (FIG. 7A) and was maintained during cooling to a temperature of about 160° C. (FIGS. 7B-7H). Crystallization occurred at about 160° C., and the cholesteric phase completely transformed to a polycrystalline phase upon reaching room temperature (FIG. 7I-7P).

A cholesteric pitch of Compound V was measured using the high-temperature wedge of FIG. 3. The measured wedge opening, β, was 1.0 mrad and the measured distance between disclination lines, S, was 4.5 mm, which resulted in a cholesteric pitch, P, of 9 μm for temperatures ranging from about 190° C. to about 160° C. Compound V formed a polycrystalline phase at room temperature.

EXAMPLE 6

Compound VI having a structure

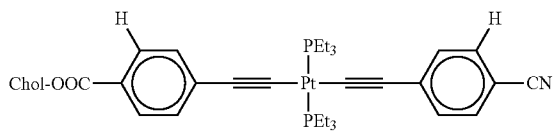

was synthesized in a manner similar to Example 1 above. The metal phosphine was [PEt$_3$]$_2$PtCl$_2$, the first a substituted ligand was cholesterol 4-ethynyl benzoate, and the second substituted ligand was 4-ethynylbenzonitrile. The percent yield of the half complex was 50.0%, and the percent yield of Compound VI was 62%.

$^{31}$P SPECTRUM: chemical shift of 1503.4 Hz and a coupling constant of 2343.8 Hz.

$^{1}$H SPECTRUM: 7.92(d, J=8.1 Hz, 2H), 7.50(d, J=8.1 Hz, 2H), 7.32(d, J=8.1 Hz, 2H), 7.31 (d, J=8.1 Hz, 2H), 5.44(d, J=2.4 Hz), 4.85(m), 2.48(d), 2.18(m, J=3.6 Hz, 12H), 1.24(m, J=7.8 Hz, 15H), 1.09(s), 0.95(d, J=6.6 Hz), 0.89(d, J=6.6 Hz), 0.71(s). $^{13}$C SPECTRUM: 166.26, 139.99, 133.87, 133.53, 132.05, 131.50, 130.80, 129.57, 127.31, 122.98. 119.84, 116.66('false t,' J=14.1 Hz), 112.91 ('false t,' J=15.1 Hz), 110.39, 109.64, 107.91, 74.60, 56.95, 56.37, 50.29, 42.57, 39.99, 39.78, 38.51, 37.31, 36.91, 36.45, 36.07, 32.20, 32.14, 28.51, 28.28, 28.17, 24.56, 24.09, 23.11, 22.84, 21.31, 19.66, 18.99, 16.63(t, J=17.6 Hz), 12.14, 8.60.

Using the cell described in Example 1, Compound VI was found to exhibit a cholesteric phase, even at room temperature (FIG. 8A-8D). As the temperature increased, a noncrystalline phase appeared (temperatures ranging from about 130° C. to about 140° C., FIGS. 8E-8J). The polycrystalline structure co-existed with the cholesteric phase in the temperatures ranging from about 130° C. to about 220° C. At about 227.8° C., the cholesteric and polycrystalline phases transition to an isotropic phase (FIG. 8K-8N), and at about 235° C., the transition to the isotropic phase was complete.

FIGS. 9A-9G illustrate cooling of Compound VI. On cooling a cholesteric phase appeared at about 240° C. (FIG. 9A) with was maintained to room temperature (FIG. 9B-9G).

A cholesteric pitch of Compound VI was twice measured using the high-temperature wedge of FIG. 3. The first measured wedge opening, β, was 1.45 mrad and the first measured distance between disclination lines, S, was 0.600 mm, which resulted in a first cholesteric pitch, P, of 1.7 μm. The second measured wedge opening, β, was 1.0 mrad and the second measured distance between disclination lines, S, was 0.800 mm, which resulted in a first cholesteric pitch, P, of 1.6 μm. The cholesteric phase of Compound VI seemed to be overcooled and existed at room temperature.

EXAMPLE 7

Compound VII having a structure

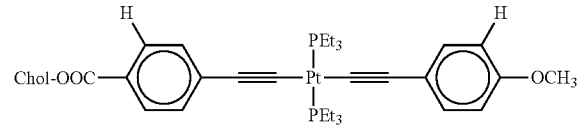

was synthesized in a manner similar to Example 1 above. The metal phosphine was [PEt$_3$]$_2$PtCl$_2$, the first a substituted ligand was cholesterol 4-ethynyl benzoate, and the second substituted ligand was 4-ethynylmethoxy benzene. The percent yield of the half complex, was 20.7 %, and the percent yield of Compound VII was 71.5%.

$^{31}$SPECTRUM: chemical shift of 1470.7 Hz and a coupling constant of 2365.1 Hz.

$^{1}$H SPECTRUM: 7.91(d, J=8.7 Hz, 2H), 7.32(d, J=8.7, 2H), 7.25(d, J=8.7 Hz, 2H), 6.80(d, J=8.7 Hz, 2H), 5.44(d, J=3.6 Hz), 4.86(m), 2.48(d), 2.20(m, J=3.6 Hz, 12H), 1.25(m, J=8.1 Hz, 15H), 1.09(s), 0.95(d, J=6.6 Hz), 0.90(dd, J=6.6 Hz, J=1.2 Hz), 0.72(s).

$^{13}$C SPECTRUM: 166.33, 157.61, 140.02, 133.92, 132.23, 130.82, 129.54, 127.03, 122.95, 121.51, 114.37('false t,' J=14.6 Hz), 113.81, 109.78, 109.43, 104.48('false t,' J=14.8 Hz), 74.53, 56.96, 56.38, 55.51, 50.29, 42.58, 40.00, 39.79, 38.52, 37.31, 36.92, 36.45, 36.08, 32.20, 32.14, 28.52, 28.30, 28.18, 24.57, 24.10, 23.12, 22.85, 21.31, 19.66, 19.00, 16.59 (t, J=17.6 Hz), 12.14, 8.63.

Figure 10A:
FIGS. 10A-10H are 500 μm×750 μm resolution micrographs of the heating of a microscopy cell filled with a Metal-PEt$_3$ complex according to another embodiment of the present invention.
Figure 10B:
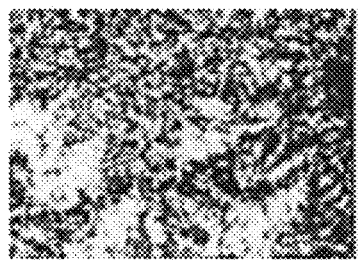
Figure 10C:
Figure 10D:
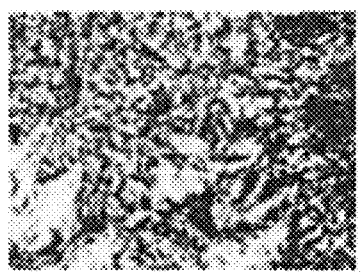
Figure 10E:
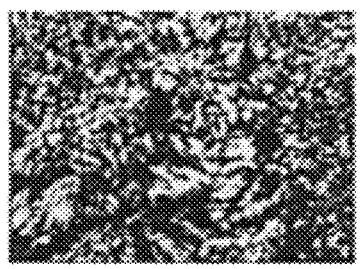
Figure 10F:
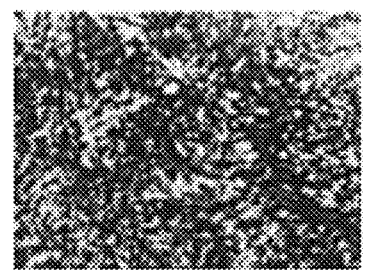
Figure 10G:
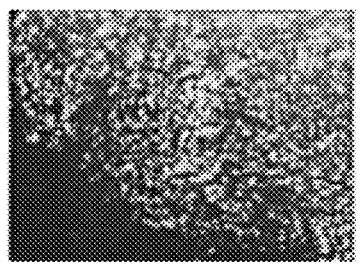
Figure 10H:
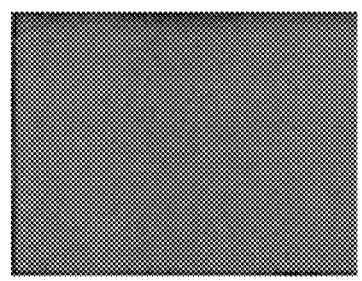

Using the cell described in Example 1, Compound VII was found to exhibit a polycrystalline phase at room temperature (FIG. 10A). As the temperature increased, the polycrystalline phase melted (about 235°, FIG. 10B-10G) and, at about 240°, melting to a poly-crystal isotropic liquid was complete (FIG. 10H).

Figure 11A:
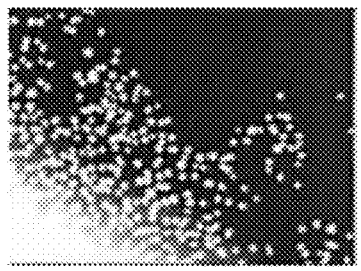
FIGS. 11A-11H are 500 μm×750 μm resolution micrographs of the cooling of the microscopy cell filled with the Metal-PEt$_3$ complex of FIGS. 10A-10H.
Figure 11B:
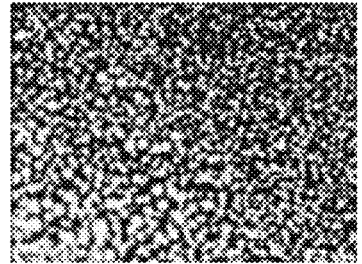
Figure 11C:
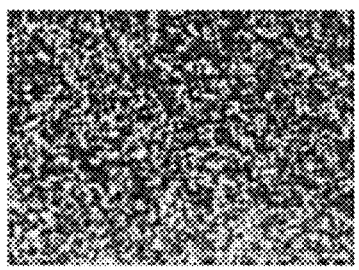
Figure 11D:
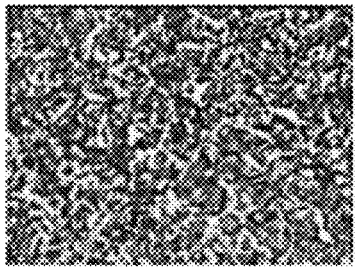
Figure 11E:
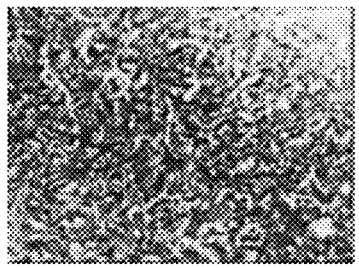
Figure 11F:
Figure 11G:
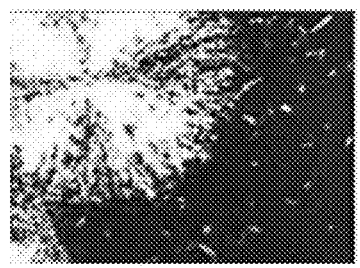
Figure 11H:
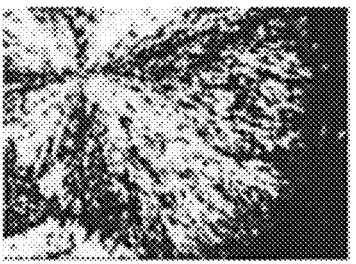

FIGS. 11A-11H illustrate cooling of Compound VII. On cooling, a cholesteric phase appeared at about 229° (FIG. 11A) and was maintained during cooling to a temperature of about 188.8° (FIG. 11B-11D). Crystallization occurred at about 188.8° C., and in about 15 minutes to about 30 minutes tire cholesteric phase transformed to a polycrystalline phase (FIGS. 11E-11H). The same polycrystalline phase was observed at room temperature (FIG. 10A).

A cholesteric pitch of Compound VII was measured using the high-temperature wedge of FIG. 3. The measured wedge opening, β, was 1.1 mrad and the measured distance between disclination lines, S, was 1.56 mm, which resulted in a cholesteric pitch, P, of 3.4 μm for temperatures ranging from about 230° C. to about 190° C. Compound VII formed a polycrystalline phase at room temperature.

EXAMPLE 8

Compound VIII having a structure

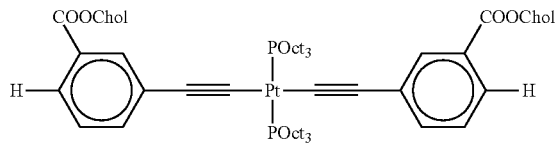

was synthesized in a manner similar to Example 1 above. The metal phosphine was [POct$_3$]$_2$PtCl$_2$ and the first and second substituted ligands were cholesterol 3-ethynyl benzoate.

$^{31}$P SPECTRUM: chemical shift of 556.2 Hz and a coupling constant of 2341.3 Hz.

$^1$H SPECTRUM: 7.96(s, 2H), 7.81(d, J=8.7 Hz, 2H), 7.44 (d, J=8.7 Hz, 2H), 7.27(t, J=8.7 Hz, 2H), 5.45(d, J=3.6 Hz,), 4.85(m, J=3.6 Hz), 2.48(d), 2.2–1.2(m), 1.1(s), 0.97(s), 0.95(s), 0.91–0.85(m), 0.72(s).

$^{13}$C SPECTRUM: 166.20, 139.90, 135.17, 132.07, 130.78, 129.39, 128.00, 126.16, 123.00, 109.83('false t,' J=14.6 Hz), 108.64, 74.64, 56.96, 56.38, 53.68, 50.30, 42.57, 40.01, 39.80, 38.52, 37.31, 36.90, 36.46, 36.10, 34.93, 32.17, 31.90, 31.57, 29.52, 28.53, 28.30, 28.18, 25.55, 24.51, 24.25, 24.11, 23.13, 22.97, 22.86, 21.32, 19.64, 18.99, 14.42, 12.12.

Using the cell described in Example 1, Compound VIII is an isotropic liquid at room temperature.

EXAMPLE 9

Compound IX having a structure

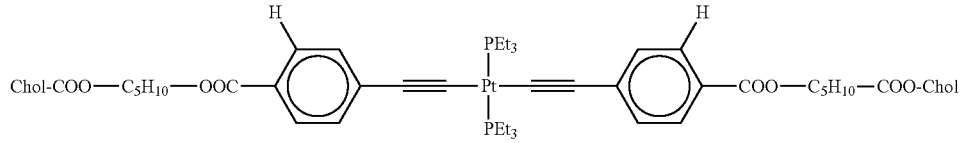

was synthesized in a manner similar to Example 1 above. The metal phosphine was [PEt$_3$]$_2$PtCl$_2$ and the first and second substituted ligands were 6-cholesteroloxy-6-oxohexyl-4-ethynylbenzoate.

$^{31}$P SPECTRUM: chemical shift of 1715.7 Hz and a coupling constant of 2312.0 Hz.

$^1$H SPECTRUM; 7.91 (d, J=8.4 Hz, 4H), 7.32(d, J=8.4 Hz, 4H), 5.38(d, J=3.9 Hz), 4.63(m, J=4.5 Hz), 4.31 (t, J=6.4 Hz), 2.36–2.14(m), 2.06–1.26(m), 1.19(q, J=8.4 Hz), 1.03(s), 0.94(s), 0.92(s), 0.88(dd, J=4.2 Hz, J'=1.2 Hz), 0.69(s).

$^{13}$C SPECTRUM: 173.20, 166.84, 139.88, 133.63, 130.68, 129.64, 127.06, 122.89, 100.67, 95.77('false t,' J=14.3 Hz). 74.06, 64.87, 56.93, 56.37, 50.26, 42.55, 39.98, 39.77, 38.40, 37.24, 36.83, 36.43, 36.05, 34.80, 32.16, 32.10, 28.73, 28.50, 28.27, 28.07, 25.90, 24.97, 24.55, 24.08, 23.11, 22.84, 21.28, 19.58, 18.98, 16.87(t, J=35.1 Hz), 12.12, 8.56(t, J=44.6 Hz).

Using the cell described in Example 1, Compound IX was found to be an isotropic liquid at room, temperature.

EXAMPLE 10

Comples X having a structure

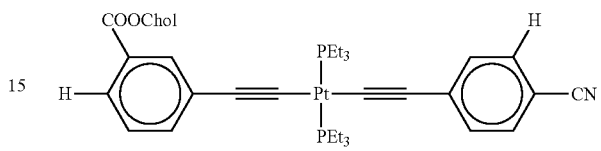

was synthesized in a manner similar to Example 1 above. The metal phosphine was [PEt$_3$]$_2$PtCl$_2$, the first substituted ligand was cholesterol 3-ethynyl benzoate, and the second substituted ligand was 4-ethynylbenzonitrile.

$^{31}$P SPECTRUM: chemical shift of 1506.5 Hz and a coupling constant of 2348.0 Hz.

$^1$H SPECTRUM: 7.95(s, 1H), 7.80(d, J=7.8 Hz, 1H), 7.48 (d, J=7.8 Hz, 2H), 4.40(d, J=9.0 Hz, 1H), 7.31(d, J=7.8 Hz, 2H), 7.26(d, J=7.8 Hz, 1H), 5.43(d, J=3.0 Hz), 4.85(m, J=4.2 Hz), 2.47(d), 2.17(m, J=3.3 Hz), 2.2–1.3(m), 1.23(t, J=8.1 Hz), 1.08(s), 0.93(d, J=6.3 Hz), 0.88(dd, J=7.5 Hz, J'J=0.9 Hz), 0.70(s).

$^{13}$C SPECTRUM: 166.2, 139.88, 135.22, 133.94, 132.15, 132.02, 131.50, 130.86, 129.05, 128.19, 126.37, 123.03, 119.79, 116.92('false t,' J=14.4 Hz), 109.45, 108.62('false t,' J=14.9 Hz), 107.85, 74.79, 56.94, 56.39, 50.28, 42.57, 39.99, 39.78, 38.48, 37.29, 36.90, 36.45, 36.07, 32.20, 32.12, 28.52, 28.28, 28.14, 24.57, 24.11, 23.13, 22.86, 21.32, 19.65, 19.00, 16.65(t, J=17.4 Hz), 12.14, 8.63.

Using the cell described in Example 1, Compound X was found to exhibit a polycrystalline phase at room temperature (FIG. 12A). As the temperature was increased, the polycrystalline phase melted (about 160° C. FIG. 12B-12E). On cooling to room temperature, Compound X showed an isotropic texture (FIG. 12F).

EXAMPLE 11

Compound XI having a structure

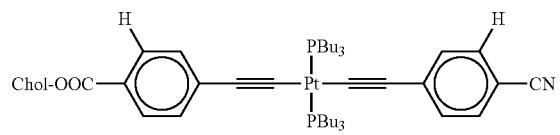

was synthesized in a manner similar to Example 1 above. The metal phosphine was [PBu$_3$]$_2$PtCl$_2$, the first a substituted ligand was cholesterol 4-ethynyl benzoate, and the second substituted ligand was 4-ethynylbenzonitrile.

$^{31}$P SPECTRUM: chemical shift of 550.1 Hz and a coupling constant of 2328.5 Hz.

$^{1}$H SPECTRUM: 7.91(d, J=8.7 Hz, 2H), 7.50(d, J=6.6 Hz, 2H), 7.30(d, J=8.7 Hz, 4H), 5.43(d, J=3.9 Hz), 4.85(m, J=3.9 Hz), 2.37(d), 2.2–1.1(m), 1.08(s), 0.91(t, J=7.2 Hz), 0.88(dd, J=6.6 Hz, J'=1.5 Hz), 0.71 (s).

$^{13}$C SPECTRUM: 166.29, 139.98, 134.02, 133.72, 132.02, 131.34, 130.69, 129.53, 127.14, 122.96, 119.86, 117.44 ('false t,' J=14.6 Hz), 113.50('false t,' J=14.6 Hz), 109.93, 109.22, 107.75, 74.56, 56.94, 56.37, 50.29, 42.57, 39.99, 39.77, 38.52, 37.31, 36.91, 36.44, 36.07, 32.20, 32.13, 28.51, 28.28, 28.18, 26.60, 24.65(t, J=6.4 Hz), 24.20(t, J=17.1 Hz), 24.09, 23.11, 22.84, 21.31, 19.65, 18.98, 14.07, 12.13.

Figure 13A:
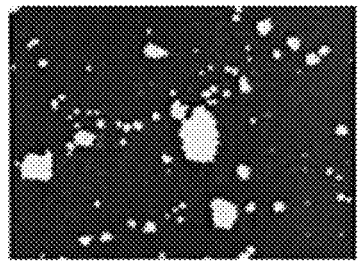
FIGS. 13A-13G are 900 μm×1200 μm resolution micrographs of the heating (FIGS. 13A-13D) and cooling (FIGS. 13E-13G) of a microscopy cell filled with a Metal-PEt$_3$ complex according to one embodiment of the present invention.
Figure 13B:
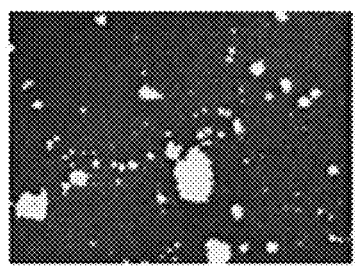
Figure 13C:
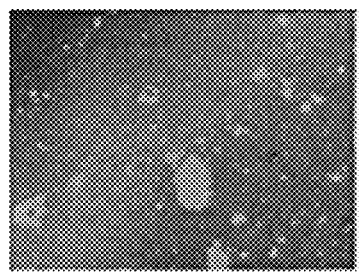
Figure 13D:
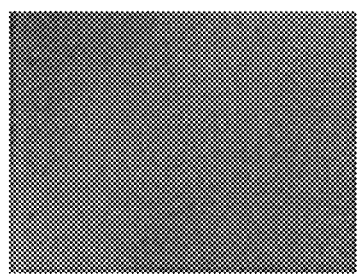
Figure 13E:
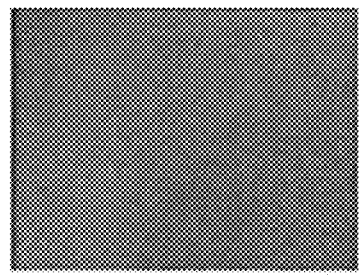
Figure 13F:
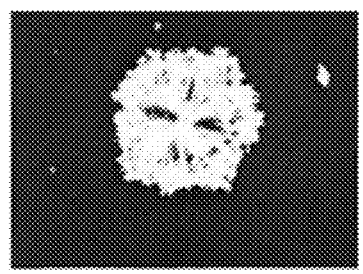
Figure 13G:
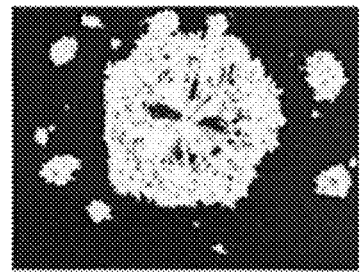

Using the cell described in Example 1, Compound XI was found to exhibit a polycrystalline phase at room temperature (FIG. 13A). As the temperature increased, the polycrystalline phase melted at a temperature ranging from about 175° C. to about 180° C. (FIGS. 13B-13D). On cooling to room temperature, Compound XI showed an isotropic texture to about 60° C. (FIG. 13E), and crystallization began at about 50° C. (FIG. 13F and 13G).

EXAMPLE 12

Compound XII having a structure

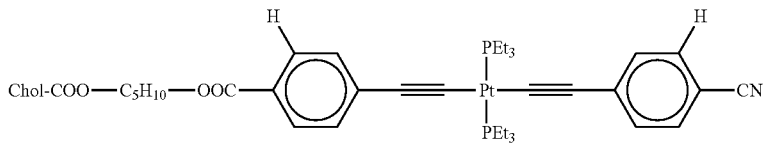

was synthesized in a manner similar to Example 1 above. The metal phosphine was [PEt$_3$]$_2$PtCl$_2$, the first a substituted ligand was 6-cholesteroloxy-6-oxohexyl-4-ethynylbenzoate, and the second substituted ligand was 4-ethynylbenzonitrile.

$^{31}$P SPECTRUM: chemical shift of 1507.0 Hz and a coupling constant of 2343.1 Hz.

$^{1}$H SPECTRUM: 7.89(d, J=8.7 Hz, 2H), 7.48(d, J=8.7 Hz), 7.30(d, J=8.7 Hz, 4H), 5.36(d), 4.62(m), 4.29(t, J=6.6 Hz), 2.31(m), 2.15(m, J=3.6 Hz), 2.1–1.3(m), 1.22(t, J=7.8 Hz), 1.01(s), 0.91(d, J=6.3 Hz), 0.86(dd, J=7.8 Hz, J'=1.2 Hz), 0.67(s).

$^{13}$C SPECTRUM: 173.16, 166.80, 139.86, 133.84, 133.68. 132.02, 131.49, 130.86, 129.57, 126.83, 122.86, 119.77, 116.60('false t,' J=14.6 Hz), 113.09('false t,' J=14.6 Hz), 110.31, 109.63, 107.90, 74.02, 64.80, 56.92, 56.35, 50.25, 42.53, 39.97, 39.76, 38.39, 37.23, 36.81, 36.43, 36.04, 34.78, 32.14, 32.08, 28.72, 28.50, 28.26, 28.06, 25.89, 24.96, 24.54, 24.07, 23.11, 22.85, 21.27, 19.60, 18.98, 16.63(t, J=10.9 Hz), 12.12, 8.61.

Using the cell described in Example 1, Compound XII was found to be an isotropic liquid at room temperature.

While the present invention has been illustrated by a description of one or more embodiments thereof and while these embodiments have been described in considerable detail, they are not intended to restrict or in any way limit the scope of the appended claims to such detail. Additional advantages and modifications will readily appear to those skilled in the art. The invention in its broader aspects is therefore not limited, to the specific details, representative apparatus and method, and. illustrative examples shown and described. Accordingly, departures may be made from such details without departing from the scope of the general inventive concept.

What is claimed is:

1. A cholesteric liquid crystal comprising:
   a metal acetylide having first and second acyl-phosphine ligands, wherein the metal is a square, planar transition metal;
   a first phenyl acetylene ligand having a first meta-or para-substituent; and
   a second phenyl acetylene ligand having a second meta-or para-ubstituent,
   wherein the first meta-or para-substituent of the first phenyl acetylene ligand is selected from the group consisting of cholesterol ester (COO-C$_{27}$H$_{45}$), cholesterol benzoate (C$_6$H$_5$-COO-C$_{27}$H$_{45}$) and 6-cholesteroloxy-6-oxohexyl-carboxyl (COO-C$_5$H$_{10}$-COO-C$_{27}$H$_{45}$).

2. The cholesteric liquid crystal of claim 1, wherein metal is platinum or palladium.

3. The cholesteric liquid crystal of claim 1, wherein the second meta-or para-subsitutent of the second phenyl acetylene ligand is selected from the group consisting of hydrogen (H), fluorine (F), cyano (CN), methoxy (OCH$_3$), cholesterol ester (COO-C$_{27}$H$_{45}$ cholesterol benzoate (C$_6$H$_5$-COO-C$_{27}$H$_{45}$), and 6-cholesteroloxy-6-oxohexyl-carboxyl-(COO-C$_5$H$_{10}$-COO-C$_{27}$H$_{45}$).

4. The cholesteric liquid crystal of claim 1, wherein the first and second acyl- phosphine ligands are selected from the group consisting of tributyl phosphine, triethyl phosphine, and trioctyl phosphine.

5. A method of forming the cholesteric liquid crystal of claim 1, the method comprising:
   selecting a metal phosphine, wherein the metal is a square, planar transition metal;
   reacting the metal phosphine with the first phenyl acetylene ligand in a two-to-one stoichiometric ratio to form a half complex;
   isolating the half complex; and
   reacting the half complex with the second phenyl acetylene ligand in a two-to-one stoichiometric ratio to form the metal acetylide.

6. The method of claim 5, wherein M is platinum or palladium.

7. The method of claim 5, further comprising:
   isolating the metal acetylide.

8. The method of claim 5, wherein isolating the half complex further comprises:
   removing a solvent; and
   isolating the half complex with chromatography.

9. A liquid crystal cell comprising:
   first and second substrates having a chamber therebetween; and
   a volume of the cholesteric liquid crystal of claim 1 filling the chamber.

10. The liquid crystal cell of claim 9, wherein each of the first and second substrates include a layer of polyimide thereon, the layer of polyimide being in contact with the volume of the cholesteric liquid crystal.

11. A cholesteric liquid crystal compound of the formula:

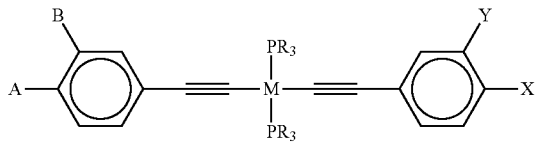

wherein M is a square, planar transition metal;
R is selected from the group consisting of butyl ($C_4H_9$), ethyl ($C_2H_5$), or octyl ($C_8H_{17}$);
X is selected from the group consisting of hydrogen (H), fluorine (F), cyano (CN), methoxy ($OCH_3$), cholesterol benzoate ($C_6H_5$-COO-$C_{27}H_4$), and (6-cholesteroloxy-6-oxohexyl-carboxyl (COO-$C_5H_{10}$-COO-$C_{27}H_{45}$); and
at least one of A, B, and Y is selected from the group consisting of cholesterol ester (COO-$C_{27}H_{45}O_2$)6-cholesteroloxy-6-oxohexyl-carboxyl (COO-$C_5H_{10}$-COO-$C_{27}H_{45}$), and cholesterol benzoate ($C_6H_5$-COO-$C_{27}H_{45}$).

12. The cholesteric liquid crystal compound of claim 11, wherein M is platinum or palladium.

13. The cholesteric liquid crystal compound of claim 11, wherein A is cholesterol ester.

14. A high-temperature wedge for use in determining a cholesteric pitch of a liquid crystal, the high-temperature wedge comprising:
a substrate; and
a silicon oxide layer on the substrate and forming an angle therewith such that a cholesteric liquid crystal resides between the silicon oxide layer and the substrate.

15. The cholesteric liquid crystal of claim 1, wherein the first meta-or para-substituent of the first phenyl acetylene ligand 6-cholesteroloxy-6-oxohexyl-carboxyl (COO-$C_5H_{10}$-COO-$C_{27}H_{45}$).

16. The cholesteric liquid crystal of claim 3, wherein the second meta-or para-substituent of the second phenyl acetylene ligand 6-cholesteroloxy-6-oxohexyl-carboxyl (COO-$C_5H_{10}$-COO-$C_{27}H_{45}$).

17. The cholesteric liquid crystal compound of claim 11, wherein X is 6-cholesteroloxy-6-oxohexyl-carboxyl (COO-$C_5H_{10}$-COO-$C_{27}H_{45}$).

18. The cholesteric liquid crystal compound of claim 11, wherein the at least one of A, B, and Y is 6-cholesteroloxy-6-oxohexyl-carboxyl (COO-$C_5H_{10}$-COO-$C_{27}H_{45}$).

* * * * *